US005534246A

United States Patent [19]
Herb et al.

[11] Patent Number: 5,534,246
[45] Date of Patent: Jul. 9, 1996

[54] TOPICALLY-EFFECTIVE COMPOSITIONS

[75] Inventors: Craig A. Herb, Chicago; Wei-Mei Sun, Palatine; Priscilla M. Walling, Darien; Susan A. Stiffe, Peoria, all of Ill.

[73] Assignee: Helene Curtis, Inc., Chicago, Ill.

[21] Appl. No.: 297,659

[22] Filed: Aug. 29, 1994

[51] Int. Cl.$^6$ .............................. A61K 7/34; A61K 7/36; A61K 7/38

[52] U.S. Cl. .............................. 424/66; 424/65; 424/67; 424/68

[58] Field of Search .................... 424/65, 66, 67, 424/68

[56] References Cited

U.S. PATENT DOCUMENTS

| | | | |
|---|---|---|---|
| 4,122,029 | 10/1978 | Gee et al. | 252/309 |
| 4,268,499 | 5/1981 | Keil | 424/68 |
| 4,311,695 | 1/1982 | Starch | 424/184 |
| 4,350,605 | 9/1982 | Hughett | 252/305 |
| 4,499,069 | 2/1985 | Krafton | 424/66 |
| 4,563,346 | 1/1986 | Decknov | 424/59 |
| 4,650,671 | 3/1987 | Golman | 424/66 |
| 4,673,570 | 6/1987 | Soldati | 424/66 |
| 4,695,451 | 9/1987 | Straw et al. | 424/47 |
| 4,704,271 | 11/1987 | Hourihan | 424/66 |
| 4,732,754 | 3/1988 | Krevald | 424/66 |
| 4,784,844 | 11/1988 | Thimineur et al. | 424/65 |
| 4,944,938 | 7/1990 | Potini | 424/68 |
| 4,948,578 | 8/1990 | Burger et al. | 424/68 |
| 4,980,156 | 12/1990 | Raleigh et al. | 424/66 |
| 4,988,504 | 1/1991 | Zotto et al. | 424/65 |
| 5,008,103 | 4/1991 | Raleigh et al. | 424/66 |
| 5,066,756 | 11/1991 | Raleigh et al. | 528/32 |
| 5,162,378 | 11/1992 | Guthauser | 514/785 |
| 5,216,033 | 6/1993 | Pereira et al. | 514/844 |
| 5,258,174 | 11/1993 | Schebece | 424/65 |
| 5,306,498 | 4/1994 | Vesperini | 424/401 |

FOREIGN PATENT DOCUMENTS

| | | |
|---|---|---|
| 0295070A2 | 12/1988 | European Pat. Off. . |
| 0396137A1 | 11/1990 | European Pat. Off. . |
| 0435483A3 | 7/1991 | European Pat. Off. . |
| 0448278A1 | 9/1991 | European Pat. Off. . |
| 2079300 | 1/1982 | United Kingdom . |
| WO91/08732 | 6/1991 | WIPO . |
| WO92/05767 | 4/1992 | WIPO . |

OTHER PUBLICATIONS

Remington's Pharmaceutical Sciences, 18th Edition 1990 p. 761.
Christiansen, "Investigations of the Optical Properties of Finely–Divided Bodies", *Annalen der Physik*, Nov. 1884, pp. 298–306 (in German and translated to English).
Garti et al., "Transparent Macroemulsions for Cosmetic Applications", *international Journal of Cosmetic Science*, 8, pp. 1–8 (1986).
Goldemberg et al., "Silicones in Clear Formulations", *D&CI*, Feb. 1986, pp. 34, 38, 40, 44.
*Cosmetics & Toiletries*, vol. 100, Dec. 1985, pp. 65–75.

Primary Examiner—C. Warren Ivy
Assistant Examiner—Evelyn Huang
Attorney, Agent, or Firm—Marshall, O'Toole, Gerstein, Murray & Borun

[57] ABSTRACT

Roll-on or gel topically-effective compositions comprising a topically-active compound, a silicon-free surfactant or silicon-free surfactant blend having an HLB value of about 0.1 to about 10, an organic phase comprising a volatile silicone compound or a volatile hydrocarbon compound, and water.

43 Claims, No Drawings

TOPICALLY-EFFECTIVE COMPOSITIONS

FIELD OF THE INVENTION

The present invention is directed to topically-effective compositions comprising a topically-active compound; a silicon-free surfactant, or blend of silicon-free surfactants, having an HLB value of about 10 or less; an organic phase comprising a volatile silicone compound or a volatile hydrocarbon compound; and water. The topically-effective compositions, like antiperspirant compositions and skin care products, are water-in-oil emulsions, and preferably are transparent. The compositions are liquid or gel-like in consistency; are phase stable; effectively deliver the topically-active compound to the skin; and exhibit excellent sensory properties. The present invention also is directed to methods of using the topically-effective compositions.

BACKGROUND OF THE INVENTION

An ideal composition for delivery of a topically-active compound to skin or hair is phase stable and delivers the topically-active compound such that it adheres to the skin or hair while topically-inactive ingredients evaporate or are otherwise removed from the application site. Topically-delivered active compounds, such as an antiperspirant compound, skin care compound or topical medicament, conventionally have been prepared as either oil-in-water emulsions or water-in-oil emulsions. However, prior topically-effective compositions prepared as emulsions typically felt wet when applied to the skin. In addition, many emulsion-type compositions leave a white, staining residue on contacted skin or clothing.

For example, antiperspirant compositions are available in a variety of forms, such as aerosol suspensions; pump sprays; roll-on powders; emulsions or suspensions; and solid gels, waxes or suspensions. Emulsified antiperspirant compositions of these various forms are well-known in the cosmetic art. Antiperspirant compositions prepared as either oil-in-water emulsions or water-in-oil emulsions typically have a milky or opaque appearance and are manufactured by complex methods. An ideal emulsified antiperspirant composition is stable for the life of the composition, effectively delivers the antiperspirant compound to the skin, does not leave a visually-observable white residue on the skin or clothing, and is esthetically pleasing to the consumer.

Roll-on and gelled emulsion-type topically-effective compositions are used by rubbing an area of the body, such as the underarm, to apply a layer of the composition to the skin. Roll-on and gel topically-effective compositions preferably possess the esthetic properties of smoothness, nonoiliness and nontackiness. The topically-effective compositions should not have a wet feeling. Clarity, or transparency, of topically-effective compositions also is a long-sought desirable esthetic property. Another highly desirable, but hard to achieve, esthetic property is avoiding a visible residue, e.g., a white layer, that is left on the skin clothing after the topically-effective composition is applied.

Nonemulsified topically-effective compositions also are known in the art but demonstrate serious disadvantages. Nonemulsified compositions often require shaking prior to each use in order to redisperse the insoluble topically-active compound that has separated from the composition. Nonemulsified topically-effective compositions that do not require shaking prior to each use, such as an antiperspirant creme or paste, typically include a relatively high percentage of suspending agents, like an organoclay. The presence of an organoclay in an antiperspirant composition is a principal source of whitening and staining skin and clothing.

Investigators have searched for topically-effective compositions, and especially transparent antiperspirant compositions, that overcome the above-described disadvantages. A roll-on antiperspirant however is difficult to formulate and manufacture because the composition requires a sufficient viscosity to adhere to the skin and resist dripping off or running down the skin, and yet is not tacky or sticky. A gel antiperspirant composition is difficult to formulate and manufacture because of formulation parameters such as firmness, viscosity control, lack of syneresis and nontackiness. Transparent, roll-on or gel antiperspirant compositions are more difficult to formulate because of the added requirement of transparency.

A transparent roll-on or gel antiperspirant composition which has consumer-acceptable esthetic and functional properties is highly desired commercially. Transparent antiperspirant compositions, especially in the roll-on or gel form, are particularly favored by consumers because such transparent products are esthetically appealing and project the appearance of product purity, safety, good performance and being non-whitening. However, providing a commercially-acceptable, transparent roll-on or gel antiperspirant composition requires overcoming several formulation and manufacturing problems.

Similarly, other roll-on or gel topically-effective compositions, especially transparent compositions, which include a topically-active compound are not readily available due to the identical formulation problems encountered in the manufacture of a roll-on or gel antiperspirant composition. Topically-effective compositions, such as skin care products, suntan lotions, topical medicaments and sunscreens, require many of the same esthetic and functional properties as an antiperspirant composition. Therefore, overcoming the formulation and manufacturing problems associated with roll-on or gel antiperspirant compositions also overcome many of the problems associated with other, related topically-effective compositions. The following discussion, which is directed primarily to antiperspirant compounds, therefore similarly is directed to gel or roll-on topically-effective compositions in general.

Solid antiperspirant compositions are divided into three main classes, i.e., compressed powder sticks, gel sticks and wax sticks. Each of these classes has advantages, but each class also has particular disadvantages. Compressed powder sticks for example frequently are brittle and hard, and leave a cosmetically-unacceptable powdery residue after application. Wax-based products often are cosmetically unacceptable because of hardness, greasiness and tackiness. The opacity of wax sticks and the visually-observable white residue remaining after application also are esthetically undesirable.

Gel-type solid antiperspirant compositions have several advantages over both compressed powder sticks and wax sticks. For example, gel antiperspirant compositions leave less residue or dust on the skin. Gel antiperspirant compositions also glide easily over the skin surface resulting in an easy and comfortable application of the composition.

Prior transparent, gel antiperspirant compositions also typically were divided into three main classes. One of these classes is the optically-clear gelled emulsion compositions. These compositions include a water phase and an oil phase. The oil phase often is suspended in the water phase (i.e., an oil-in-water emulsion) by using a sufficient amount of an appropriate emulsifier or emulsifiers. Oil-in-water emulsion products have a wet feel because the continuous external phase is aqueous. Water-in-oil emulsions, wherein the continuous external phase is organic in nature, also are known. The emulsions conventionally contained waxes, silicones, clays and emollients. Gelled emulsion compositions, including optically-clear compositions, are illustrated in U.S. Pat. Nos. 4,673,570, 4,268,499, and 4,350,605; and in "Deodorant and Antiperspirant Formulary", *Cosmetics & Toiletries*, Dec. 12, 1985, vol. 100, p. 65–75.

The optically-clear gelled emulsion compositions often exhibit the disadvantages of composition instability during storage; the development of a hazy or milky appearance during storage; a stringy, tacky, oily consistency and other undesirable esthetic properties. In addition, the emulsion gel compositions often leave a visible residue on the skin or clothing in the form of a white layer.

Another disadvantage of optically-clear gelled emulsion compositions is the complex method of preparing an optically-clear gelled emulsion composition. The method traditionally requires high shear rates during mixing, high processing temperatures, and a series of cooling and heating process steps. In one embodiment of the present invention, optically-clear gel-like emulsion compositions are prepared by a simple refractive index matching technique to provide topically-effective compositions that overcome the above-described disadvantages of prior optically-clear gelled emulsion compositions.

The problems associated with gel antiperspirants can be partially overcome by formulating a roll-on antiperspirant. Roll-on antiperspirants typically are viscous liquids to semisolids However, roll-on antiperspirants often impart a tacky feel and still have a tendency to leave an unsightly white residue on the skin.

Numerous patents and publications disclose attempts to provide a consumer-acceptable, roll-on or gel topically-effective composition, and especially an antiperspirant composition. EP 0 396 137 discloses a transparent, anhydrous antiperspirant composition wherein transparency is accomplished by matching the refractive index of the anhydrous vehicle with a particulate antiperspirant compound. EP 0 435 483 discloses a water-in-oil silicone emulsion including an alkane diol and an inorganic electrolyte. WO 91/08732 and WO 92/05767 disclose emulsified, water-in-oil antiperspirant compositions having a viscosity of less than about 1,000 cps (centipoise) or at least about 50,000 cps, respectively. U.S. Pat. Nos. 4,311,695, 4,980,156, 4,988,504 and 5,066,756 disclose opaque, water-in-oil antiperspirant emulsions. Each reference relies upon a silicon-containing emulsifier to provide the water-in-oil emulsion.

U.S. Pat. No. 4,948,578 discloses optically clear antiperspirant sticks comprising up to 50% water and a surfactant having a high HLB value. U.S. Pat. No. 5,258,174 also discloses clear stick antiperspirant compositions. U.S. Pat. No. 4,499,069 discloses an antiperspirant composition having a specific combination of a high HLB surfactant and a low HLB surfactant to provide a surfactant blend having an HLB of about 7.5 to less than 9.9. U.S. Pat. No. 5,216,033 discloses a transparent water-in-oil emulsion prepared from a silicone surfactant, wherein the refractive index is matched using a polyhydric alcohol. U.S. Pat. No. 4,944,938 discloses a transparent antiperspirant gel including only 15% to 20% water.

GB 2,079,300 discloses transparent silicone-containing oil-in-water emulsions prepared by the addition of a polyol. The emulsions include high HLB surfactants. U.S. Pat. No. 4,784,844 discloses oil-in-water opaque to transparent silicone emulsions including up to 80% internal phase. Other patents disclosing silicone-containing oil-in-water emulsions include U.S. Pat. Nos. 4,122,029, 4,732,754, and 5,162,378. Patents disclosing silicone surfactants used in topically-effective compositions include U.S. Pat. Nos. 4,988,504 and 5,008,103.

Other patents and publications disclosing emulsified antiperspirant compositions include U.S. Pat. Nos. 4,695,451 and 4,650,671; EP 0 295 070 and EP 0 448 278; R. L. Golemberg et al., "Silicones in Clear Formulations", D&CI, February, 1986, pages 34, 38, 40 and 44; and N. Garti et al., "Transparent Microemulsions for Cosmetic Preparations", *Internat. J. Cosmet. Sci.*, 8, pp. 1–8 (1986).

Although numerous patents disclose transparent antiperspirant compositions, the compositions designated as clear or transparent often lack the clarity or the dry feel desired by consumers. Some transparent antiperspirant compositions also exhibit an unacceptable degree of syneresis, or phase separation, during storage. Moreover, many of the prior art transparent compositions become cloudy or hazy after standing for a period of time. Typically, haziness increases to such an extent that the composition is cloudy and has little or no transparency about a month after preparation. Antiperspirant compositions conventionally have a product life in excess of one month. Therefore, the length of time the composition retains its transparency is an important esthetic property.

Investigators continually have sought to provide emulsion-type roll-on or gel topically-effective compositions having both long-term stability and sufficient esthetic and functional properties for consumer acceptance. These esthetic and functional properties include transparency, no visually-observable whitening of the skin and clothing, and the ability to effectively deliver the topically-active compound to the skin without irritating the skin or imparting a tacky or sticky feeling. The present invention is directed to providing roll-on or gel topically-effective compositions, and preferably transparent compositions, exhibiting these consumer-acceptable esthetic and functional properties.

SUMMARY OF THE INVENTION

The present invention is directed to roll-on or gel topically-effective compositions having improved efficacy and esthetics, and to methods of using the topically-effective compositions. More particularly, the present invention is directed to a roll-on or gel topically-effective composition comprising a topically-active compound, like an antiperspirant compound, a skin care compound or a topical medicament; a silicon-free surfactant or surfactant blend having an HLB value of about 10, preferably about 7, or less; an organic phase comprising a volatile silicone compound or a volatile hydrocarbon compound; and water. Preferably, the topically-effective compositions are transparent.

The "HLB value", or hydrophobic-lipophilic balance value, of a surfactant is a term well-known to those skilled in the art. The HLB value is related to the solubility of the surfactant, wherein a surfactant with a low HLB value, e.g., about 10 or less, tends to be oil soluble and a surfactant with a high HLB value, e.g., greater than about 10, tends to be water soluble.

In particular, the roll-on or gel topically-effective compositions comprise:

(a) about 65% to about 99.5% by weight of an aqueous phase comprising (i) a topically-active compound and (ii) water;

(b) about 0.5% to about 35% by weight of an organic phase comprising volatile silicone compound, a volatile hydrocarbon compound, or a mixture thereof; and (c) about 0.1% to about 15% by weight of a surfactant phase consisting essentially of a surfactant or a surfactant blend, wherein the surfactant or surfactant blend is free of silicon and has an HLB value of about 10 or less. The topically-effective compositions optionally include a compound, and typically a water-soluble compound, to adjust the refractive index of the first phase (e.g., the aqueous phase) to match the refractive index of the second phase (e.g., the organic phase), and thereby provide a transparent composition.

The roll-on or gel topically-effective compositions maintain composition clarity over extended storage periods, can be essentially nonstaining and nonwhitening to skin and clothing, effectively deliver the topically-active compound to the skin, and exhibit excellent esthetic and functional properties, including sensory properties, for consumer acceptance. The present topically-effective compositions remain transparent for at least six months when stored at room temperature.

To achieve transparency, a sufficient amount of a refractive index-adjusting compound is included in either the aqueous phase or the organic phase to match the refractive indices of the aqueous phase and the organic phase. Generally, the refractive index-adjusting compound is water soluble and is included in the aqueous phase.

If the refractive indices of the aqueous phase and the organic phase are essentially matched at all wavelengths, the topically-effective composition is transparent. If the optical dispersion differs between the two phases and the refractive indices of the two phases are essentially matched at a single wavelength, then the topically-effective composition is transparent, but transmits light of a particular wavelength and accordingly is colored. In the absence of refractive index matching, the present compositions are opaque, but nevertheless exhibit all other advantages of the present invention.

In one important embodiment, the refractive indices of the aqueous phase and organic phase are matched by adding calcium chloride to the aqueous phase. Surprisingly, incorporating calcium chloride in the aqueous phase of a topically-effective composition of the present invention reduces the skin irritancy potential of the topically-effective composition.

A topically-effective composition of the present invention is a liquid or a flowable semisolid composition comprising a topically-active compound and having a viscosity of about 1,000 cps to about 100,000 cps (centipoise), and preferably about 1,500 to about 40,000 cps. To achieve the full advantage of the present invention, the topically-effective composition has a viscosity of about 1,500 to about 5,000 cps. Compared to prior roll-on and gel compositions, the present topically-effective compositions effectively resist coalescence and phase separation, or syneresis, over a prolonged storage period. Other undesirable esthetic properties which are reduced or eliminated by a composition of the present invention include a feeling of wetness and the long drying times caused by high percentages of traditional emollients and polyols, and whitening and staining of skin and clothing caused by organoclay suspending agents.

In one important embodiment, a topically-effective composition of the present invention incorporates an astringent salt as the topically-active compound to form a stable and efficacious antiperspirant composition. In other embodiments of the present invention, the topically-effective composition incorporates topically-effective drugs and medicaments; topical anesthetics; sunscreen agents; skin care agents; skin-soothing emollients and other topical cosmetic compounds; topical anti-inflammatories; and the like. The topically-active compound incorporated into the compositions of the present invention preferably is incorporated into the aqueous phase, but can be incorporated into the organic phase.

In a preferred embodiment, a transparent roll-on or gel topically-effective composition comprises:

(a) about 80% to about 98% by weight of an aqueous phase, said aqueous phase comprising (i) water and (ii) a topically-effective amount of a topically-active compound, typically about 0.1% to about 40% by weight based on the total weight of the topically-effective composition;

(b) about 2% to about 20% by weight of an organic phase comprising a volatile silicone compound, a volatile hydrocarbon compound, or a mixture thereof;

(c) about 0.5% to about 5% by weight of a surfactant phase consisting essentially of a silicon-free surfactant, or a silicon-free surfactant blend, having an HLB value of about 1 to about 7; and (d) optionally, a sufficient amount of a refractive index-adjusting compound to adjust and match the refractive indices of the aqueous phase and the organic phase.

In another preferred embodiment, the transparent, topically-effective composition is a water-in-oil, roll-on or gel antiperspirant composition, which incorporates calcium chloride as the refractive index-adjusting compound, and which has a reduced skin irritancy potential.

Other aspects of the present invention include providing a topically-effective composition for the administration of topically-active compounds, such as topical drugs and medicaments, topical anesthetics, sunscreen agents, skin care agents, and other topical cosmetic compounds, topical anti-inflammatories and the like, by incorporating the topically-active compound in compositions of the present invention.

The above and other advantages and novel features of the present invention will become apparent from the following detailed description of the preferred embodiments.

DETAILED DESCRIPTION OF THE PREFERRED EMBODIMENTS

A stable topically-effective composition of the present invention is a water-in-oil emulsion comprising a topically-active compound, such as an antiperspirant compound, like an astringent salt; a silicon-free surfactant, or silicon-free surfactant blend, having an HLB value of about 10 or less, and preferably about 7 or less; an organic phase comprising a volatile silicone compound, a volatile hydrocarbon compound, or a mixture thereof; and water. The topically-effective composition is a liquid or a flowable semisolid composition having a viscosity in the range of about 1,000 to about 100,000 cps and that is applied to the skin or hair. The organic phase and the water evaporate leaving the topically-active compound and other nonvolatile composition ingredients in contact with the skin or hair.

In accordance with an important feature of the present invention, the liquid or flowable semisolid composition is a stable emulsion that effectively resists coalescence and phase separation, or syneresis, over long storage periods. Therefore, the topically-effective composition is available for immediate application to the skin or hair without the need to vigorously shake or agitate the composition in order to redisperse the composition ingredients throughout the composition prior to use.

In particular, the roll-on or gel topically-effective compositions comprise:

(a) about 65% to about 99.5% by weight of an aqueous phase comprising (i) water and (ii) a topically-effective amount of a topically-active compound, typically about 0.1% to about 40% by weight based on the total weight of the topically-effective composition;

(b) about 0.5% to about 35% by weight of an organic phase comprising a volatile silicone compound, a volatile hydrocarbon compound, or a mixture thereof;

(c) about 0.1% to about 15% by weight of a surfactant phase consisting essentially of a surfactant, or surfactant blend, having an HLB value of about 10 or less, and preferably about 7 or less, wherein the surfactant or surfactant blend is free of silicon; and (d) optionally, a sufficient amount of a refractive index-matching compound capable of matching the refractive index of the aqueous phase and the refractive index of the organic phase. Preferably, the refractive index-matching compound is water soluble, and the topically-effective compositions are transparent.

As used here and hereinafter, the term "transparent" is defined as at least 50% transmittance determined spectrophotometrically at 700 nm (nanometers). The transparency of the topically-effective compositions can be determined spectrophotometrically by measuring % transmittance at 700 nm (nanometers), using water as the standard for 100% transmittance.

The transparent roll-on or gel topically-effective compositions are stable to phase separation, do not become hazy or milky during storage, and exhibit exceptional esthetic and functional properties. The topically-effective compositions are liquids or flowable semisolids, are capable of effectively delivering the topically-active compound to the skin, and in preferred embodiments are essentially nonwhitening, i.e., do not leave a visually-observable white residue on the skin or clothing.

I. The Aqueous Phase

The aqueous phase of the present topically-effective compositions comprise water and a topically-active compound. The aqueous phase can further comprise an optional water-soluble compound capable of matching the refractive index of the aqueous phase to the refractive index of the organic phase. The aqueous phase is about 65% to about 99.5%, and preferably about 80% to about 98%, by weight of the composition.

The aqueous phase is the internal phase of a water-in-oil emulsion of the present invention. Surprisingly, although the internal aqueous phase constitutes 65% to 99.5% by weight of the present topically-effective compositions, the relatively small amount of external organic phase gives the compositions the esthetic feeling of an oil-based composition upon application. Therefore, the present compositions provide the esthetic benefits of an oil-based composition, yet are substantially more economical because of the high percentage of aqueous phase in the composition.

a. Topically-Active Compounds

In accordance with an important feature of the present invention, a wide variety of topically-active compounds can be incorporated into a topically-effective composition of the present invention. Such topically-active compositions include both cosmetic and medicinal compounds that act upon contact with the skin or hair. The topically-active compound is present in a sufficient amount to perform its intended function, typically in an amount of about 0.1% to about 40% by weight of the composition.

In accordance with another important feature of the present invention, the topically-active compound can be incorporated into the aqueous phase or into the organic phase of the composition. Whether a particular topically-active compound is incorporated into the aqueous phase or the organic phase of the compositions is related to the solubility of the topically-active composition in water. In a preferred embodiment, the topically-active compound is incorporated into the aqueous phase.

In addition, a first topically-active compound can be incorporated into the aqueous phase and a second topically-active compound can be incorporated into the organic phase to achieve enhanced efficacy (e.g., the composition includes a medicament in each phase) or to provide different benefits (e.g., the composition includes a medicament in one phase and a topical anesthetic in the second phase). In each embodiment, the topically-effective composition of the present invention is resistant to composition separation and effectively applies the topically-active compound to the skin or hair.

The topically-active compound can be a cosmetic compound, a medically-active compound or any other compound that is useful upon application to the skin or hair. Such topically-active compounds include antiperspirants, skin care compounds, antibacterial compounds, antifungal compounds, anti-inflammatory compounds, topical anesthetics, sunscreens and other cosmetic and medical topically-effective compounds.

In accordance with an important feature of the present invention, the topically-effective composition is an antiperspirant composition including any of the antiperspirant compounds known in the art, such as the astringent salts. The astringent salts include organic and inorganic salts of aluminum, zirconium, zinc, and mixtures thereof. The anion of the astringent salt can be, for example, sulfate, chloride, chlorohydroxide, alum, formate, lactate, benzyl sulfonate or phenyl sulfonate. Exemplary classes of antiperspirant astringent salts include aluminum halides, aluminum hydroxyhalides, zirconyl oxyhalides, zirconyl hydroxyhalides, and mixtures thereof.

Exemplary aluminum salts include aluminum chloride and the aluminum hydroxyhalides having the general formula $Al_2(OH)_xQ_y \cdot XH_2O$, wherein Q is chlorine, bromine or iodine; x is about 2 to about 5; x+y is about 6, wherein x and y are not necessarily integers; and X is about 1 to about 6. Exemplary zirconium compounds include zirconium oxy salts and zirconium hydroxy salts, also referred to as zirconyl salts and zirconyl hydroxy salts, and represented by the general empirical formula $ZrO(OH)_{2-nz}L_z$, wherein z varies from about 0.9 to about 2 and is not necessarily an integer; n is the valence of L; 2–nz is greater than or equal to 0; and L is selected from the group consisting of halides, nitrate, sulfamate, sulfate, and mixtures thereof.

The antiperspirant compound is present in the roll-on or gelled antiperspirant composition in an amount of about 1% to about 40%, and preferably about 5% to about 30%, by weight of the composition. To achieve the full advantage of the present invention, the antiperspirant compound is present in an amount of about 10% to about 25% by weight of the antiperspirant composition.

The antiperspirant compounds are water-soluble. Exemplary antiperspirant compounds therefore include, but are not limited to, aluminum bromohydrate, potassium alum, sodium aluminum chlorohydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof. Numerous other useful antiperspirant compounds are listed in WO 91/19222 and in the *Cosmetic and Toiletry Fragrance Handbook*, The Cosmetic, Toiletry and Fragrance Association, Inc., Washington, D.C., p. 56, 1989, hereinafter the *CTFA Handbook*, incorporated herein by reference.

Preferred antiperspirant compounds are the aluminum-zirconium chlorides complexed with an amino acid, like glycine, and the aluminum chlorohydrates. Preferred aluminum-zirconium chloride glycine complexes have an aluminum (Al) to zirconium (Zr) ratio of about 1.67 to about 12.5, and a total metal (Al+Zr) to chlorine ratio (metal to chlorine) of about 0.73 to about 1.93.

In addition to antiperspirant compounds, other topically-active compounds can be included in the compositions of the present invention in an amount sufficient to perform their intended function. For example, if the topically-effective composition is intended to be a sunscreen, then compounds such as benzophenone-4, diethanolamine methoxycinnamate, p-aminobenzoic acid, phenylbenzimidazole sulfonic acid or triethanolamine salicylate can be incorporated into the aqueous phase.

Further, sunscreen compounds such as dioxybenzone, ethyl 4-[bis(hydroxypropyl)]aminobenzoate, glyceryl aminobenzoate, homosalate, menthyl anthranilate, octocrylene, octyl methoxycinnamate, octyl salicylate, oxybenzone, padimate O, red petrolatum, titanium dioxide, 4-menthylbenzylidene camphor, benzophenone-1, benzophenone-2, benzophenone-6, benzophenone-12, isopropyl dibenzoyl methane, butyl methoxydibenzoylmethane, zotocrylene, or zinc oxide can be incorporated into the organic phase. Other sunscreen compounds soluble in either the aqueous or organic phase are listed in *CTFA Cosmetic Ingredient Handbook*, First Ed., The Cosmetic, Toiletry and Fragrance Assn., Inc., Washington, D.C. (1988), pages 86 and 87 (hereinafter *CTFA Handbook*), incorporated herein by reference.

Similarly, topically-active drugs, like antifungal compounds; antibacterial compounds; anti-inflammatory compounds, topical anesthetics; skin rash, skin disease and dermatitis medications; and anti-itch and irritation-reducing compounds can be included in the compositions of the present invention. For example, analgesics such as benzocaine, dyclonine hydrochloride, aloe vera and the like; anesthetics such as butamben picrate, lidocaine hydrochloride, xylocaine and the like; antibacterials and antiseptics, such as povidone-iodine, polymyxin b sulfate-bacitracin, zinc-neomycin sulfate-hydrocortisone, chloramphenicol, methylbenzethonium chloride, and erythromycin and the like; antiparasitics, such as lindane; deodorants, such as chlorophyllin copper complex, aluminum chloride, aluminum chloride hexahydrate, and methylbenzethonium chloride; essentially all dermatologicals, like acne preparations, such as benzoyl peroxide, erythromycin-benzoyl peroxide, clindamycin phosphate, 5,7-dichloro-8-hydroxyquinoline, and the like; anti-inflammatory agents, such as alclometasone dipropionate, betamethasone valerate, and the like; burn relief ointments, such as o-amino-p-toluenesulfonamide monoacetate and the like; depigmenting agents, such as monobenzone; dermatitis relief agents, such as the active steroid amcinonide, diflorasone diacetate, hydrocortisone, and the like; diaper rash relief agents, such as methylbenzethonium chloride and the like; emollients and moisturizers, such as mineral oil, PEG-4 dilaurate, lanolin oil, petrolatum, mineral wax and the like; fungicides, such as butocouazole nitrate, haloprogin, clotrimazole, and the like; herpes treatment drugs, such as O-[(2-hydroxyethoxy)methyl]guanine; pruritic medications, such as alclometasone dipropionate, betamethasone valerate, isopropyl myristate MSD, and the like; psoriasis, seborrhea and scabicide agents, such as anthralin, methoxsalen, coal tar and the like; steroids, such as 2-(acetyloxy)-9-fluoro-1',2',3',4'-tetrahydro-11-hydroxypregna-1,4-dieno[16,17-b]naphthalene-3, 20-dione and 21-chloro-9-fluoro-1',2',3',4'-tetrahydro-11b-hydroxypregna-1,4-dieno[16z,17-b]naphthalene-3,20-dione. Any other medication capable of topical administration also can be incorporated in a composition of the present invention in an amount sufficient to perform its intended function. Other topically-active compounds are listed in *Remington's Pharmaceutical Sciences*, 17th Ed., Merck Publishing Co., Easton, Pa. (1985), pages 773–791 and pages 1054–1058 (hereinafter *Remington's*), incorporated herein by reference.

b. Water

Sufficient water is present in the aqueous phase such that the aqueous phase comprises about 65% to about 99.5% by weight of the topically-effective composition. Therefore, water is present in the topically-effective composition in an amount of about 25% to about 99.4%, and typically in an amount of about 40% to about 95%, by weight of the composition. The inclusion of a water-soluble compound in the aqueous phase to match refractive indices of the aqueous phase and organic phase generally lowers the amount of water in the composition to about 35% to about 80% by weight of the composition.

c. Optional Ingredients

The aqueous phase also can include optional ingredients traditionally included in topically-effective compositions. These optional ingredients include, but are not limited to, dyes, fragrances, preservatives, antioxidants, detackifying agents, deodorizing agents, and similar types of compounds. The optional ingredients are included in the topically-effective compositions in an amount sufficient to perform their intended function.

As discussed hereinafter in detail, the aqueous phase also can include a compound that increases the refractive index of the aqueous phase to match the refractive index of the organic phase. Accordingly, the topically-effective composition then is transparent, and can be colored due to Christiansen effect described in Christiansen, *Annalen der Physik*, (Nov. 1884), pp. 298–306.

II. The Organic Phase

A topically-effective composition of the present invention also comprises about 0.5% to about 35%, and preferably about 2% to about 20%, by weight of an organic phase. The components of the organic phase improve the feel of the topically-effective composition on the skin, allow easier application of the topically-effective composition to the skin, and allow the skin to feel dry more quickly after application of the topically-effective composition. Other compounds included in the organic phase can reduce or eliminate the occurrence of a visible white residue on the skin after topical application.

As described in more detail hereinafter, the organic phase is the continuous phase of a water-in-oil emulsion of the present invention, and therefore gives the topically-effective composition a dry feeling upon application. The organic phase evaporates thereby leaving the topically-active compound and other nonvolatile components in contact with the skin. The oil phase imparts a dry feeling even though the organic phase constitutes only 0.5% to 35% by weight of the composition.

The organic phase comprises a volatile silicone compound, a volatile hydrocarbon compound or a mixture thereof. Preferably, the organic phase comprises a volatile silicone compound. The organic phase also can include a nonvolatile organic compound or a topically-active compound in a sufficient amount to impart a particular functional or esthetic effect (e.g., emolliency) without adversely affecting the topically-effective composition (e.g., imparting emulsion instability). Although the organic phase can incorporate a topically-active compound, the topically-active compound preferably is incorporated into the aqueous phase.

Exemplary volatile organic compounds present in the organic phase of the present invention include the volatile, low molecular weight polydimethylsiloxane compounds. The volatile, low molecular weight polydimethylsiloxane compound can be either a linear or a cyclic polydimethylsiloxane compound, as long as the polydimethylsiloxane compound has sufficient volatility to volatilize from the skin after topical application of the composition onto the skin. Preferably the polydimethylsiloxane is a cyclic siloxane, like cyclomethicone. The volatile silicones feel very rich as they are applied to the skin, but then evaporate relatively quickly to leave only the nonvolatile components of the composition on the skin. In general, volatile polydimethylsiloxane compounds useful in the compositions of the present invention include polydimethylsiloxane compounds having a viscosity of about 0.5 cs (centistokes) to about 10 cs. The preferred volatile polydimethylsiloxanes have a viscosity in the range of from about 0.5 cs to about 6 cs.

The cyclic, low molecular weight, volatile polydimethylsiloxanes, designated in the *CTFA International Cosmetic Ingredient Dictionary*, 4th Ed., Cosmetic, Toiletry and Fragrance Association, Washington, D.C. (1991) (hereinafter *CTFA Dictionary*) as cyclomethicones, are the preferred siloxanes used in a composition of the present invention. To achieve the full advantage of the present invention, a cyclomethicone used in a composition of the present invention is a low viscosity, low molecular weight, water-insoluble cyclic compound having an average of about 3 to about 6 —[O—Si(CH$_3$)$_2$]— repeating group units per molecule (hexamethylcyclotrisiloxane, octamethylcyclotetrasiloxane, decamethylcyclopentasiloxane, dodecamethylcylcohexasiloxane, and mixtures thereof); boil at atmospheric pressure at about 150° C. to about 250° C.; and have a viscosity at 25° C. of about 2 to about 6 centistokes. The polydimethyl cyclosiloxanes having an average of about 4 to about 5 repeating units per molecule, i.e., the tetramer and pentamer, are especially preferred. Suitable cyclomethicones are available commercially under the tradenames DOW CORNING 245 FLUID, DOW CORNING 344 FLUID and DOW CORNING 345 FLUID from Dow Corning Corporation, Midland, Mich., and SILICONE SF-1173 and SILICONE SF-1202 from General Electric, Waterford, N.Y.

An example of a linear, low molecular weight, volatile polydimethylsiloxane compound useful in the composition and method of the present invention is the compound designated in the *CTFA Dictionary* as hexamethyldisiloxane, available commercially under the tradename DOW CORNING 200 FLUID from Dow Corning Corp., Midland, Mich.

Hexamethyldisiloxane has a viscosity of 0.65 cs, is highly volatile, is non-greasy, and provides lubrication for topical application to the composition of the present invention to the skin. Other linear polydimethylsiloxanes, such as decamethyltetrasiloxane, having a boiling point of about 195° and a viscosity of 1.5 cs; octamethyltrisiloxane; and dodecamethylpentasiloxane, also have sufficient volatility to be useful in the composition of the present invention. Another useful linear siloxane is bisphenylhexamethicone. In general, it has been found that a linear, low molecular weight volatile polydimethylsiloxane compound having a viscosity at 25° C. and atmospheric pressure of about 0.5 cs to about 5 cs, and a boiling point at atmospheric pressure of about 100° C. to about 250° C., is preferred for use in the composition and method of the present invention.

The organic phase of a composition of the present invention also can comprise a volatile hydrocarbon compound, such as a hydrocarbon having about 10 to about 30 carbon atoms, that has sufficient volatility to slowly volatilize from the skin or hair after application of the topically-effective composition. The volatile hydrocarbon compounds provide essentially the same benefits as the volatile silicone compounds, such as lubrication and a rich feel during application.

Volatile hydrocarbon compounds incorporated into the transparent antiperspirant composition include, for example, isododecane and isohexadecane, i.e.,. PERMETHYL 99A, PERMETHYL 101A and PERMETHYL 102A, available from Presperse, Inc., South Plainfield, N.J. A preferred volatile hydrocarbon compound is an aliphatic hydrocarbon having about 12 to about 24 carbon atoms, and having a boiling point of about 100° C. to about 250° C. One such compound is ISOPAR M (a $C_{13}$–$C_{14}$ isoparaffin available from Exxon Chemical Co., Baytown, Tex.). Other exemplary volatile hydrocarbon compounds are depicted in general structural formula (I), wherein n ranges from 2 to 5.

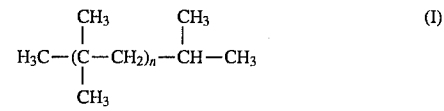

Nonvolatile organic compounds also can be incorporated into the organic phase. The nonvolatile organic compound can be a topically-active compound, can provide an esthetic effect or can adjust the refractive index of the organic phase to match the refractive index of the aqueous phase. For example, a mineral oil can be incorporated into the organic phase to reduce or eliminate a visible white residue on the skin after topical application. A phenyltrimethicone or a polydimethylsiloxane having a viscosity at 25° C. of about 6 to about 400 cs, such as DOW CORNING 556 FLUID or DOW CORNING 200 FLUID, respectively, available from Dow Corning Corp., Midland, Mich., can be added to the organic phase to adjust the refractive index of organic phase.

Other exemplary nonvolatile organic compounds that can be incorporated into the organic phase include, but are not limited to, (1) branched 1-decene oligomers, like 1-decene dimer or a polydecene; or (2) water-insoluble emollients, such as an ester having at least about 10 carbon atoms, and preferably about 10 to about 32 carbon atoms. Suitable esters include those comprising an aliphatic alcohol having about eight to about twenty carbon atoms and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight-chained or branched.

Preferably, the ester has a molecular weight of less than about 500 and provides emollient properties. Suitable esters therefore include, for example, but are not limited to:

(a) aliphatic monohydric alcohol esters,
   myristyl propionate,
   isopropyl isostearate,
   isopropyl myristate,
   isopropyl palmitate,
   cetyl acetate,
   cetyl propionate,
   cetyl stearate,
   isodecyl neopentanoate,
   cetyl octanoate,
   isocetyl stearate;

(b) aliphatic di- and tri-esters of polycarboxylic acids, including but not limited to:
   diisopropyl adipate,
   diisostearyl fumarate,
   dioctyl adipate, and
   triisostearyl citrate;

(c) aliphatic polyhydric alcohol esters, including but not limited to:
   propylene glycol dipelargonate;

(d) aliphatic esters of aromatic acids, including but not limited to:
   $C_{12}$–$C_{15}$ alcohol esters of benzoic acid,
   octyl salicylate,
   sucrose benzoate, and
   dioctyl phthalate.

Numerous other esters are listed in the *CTFA Handbook,* at pages 24 through 26, incorporated herein by reference.

III. The Surfactant Phase

The topically-effective composition of the present invention also includes about 0.1% to about 15%, and preferably about 0.1% to about 10%, of a surfactant phase. To achieve the full advantage of the present invention the composition has about 0.5% to about 5% of the surfactant phase.

The surfactant phase consists essentially of a surfactant, or a blend of surfactants, having an HLB value of about 10 or less (i.e., an HLB value of about 0.1 to about 10). Preferably, the surfactant phase has an HLB value of about 1 to about 7. To achieve the full advantage of the present invention, the surfactant phase has an HLB value of about 3 to about 6. In accordance with an important feature of the present invention, the surfactant phase is free of silicon.

Therefore, the surfactant phase consists essentially of a silicon-free surfactant having an HLB value of about 0.1 to about 10, or a blend of silicon-free surfactants having different HLB values such that the blend has an HLB value of about 1 to about 10. A surfactant phase having an HLB value of about 0.1 to about 10 provides a water-in-oil emulsion.

A silicon-free surfactant having an HLB value of about 0.1 to about 10 can be used alone as the surfactant phase of the present invention. The surfactant phase also can comprise a blend of silicon-free surfactants each having an HLB value of less than 10. In addition, silicon-free surfactants having an HLB value of about 0.1 to about 10 also can be used as the first surfactant of a silicon-free surfactant blend having an HLB value of about 1 to about 10, then a silicon-free surfactant having an HLB of greater than about 10 is the second surfactant of the silicon-free surfactant blend having an HLB of about 1 to about 10.

Typically, nonionic surfactants having an HLB value of about 10 or less have a hydrophobic moiety, such as a long chain alkyl group or an alkylated aryl group, and a hydrophilic chain comprising a small number (i.e., one to about six) of ethoxy and/or propoxy moieties. The silicon-free surfactants having an HLB of greater than about 10 typically have the same type hydrophobic moiety as the low HLB surfactants, but include more ethoxy and/or propoxy moieties.

The HLB value of a particular surfactant can be found in *McCutcheon's Emulsifiers and Detergents, North American and International Editions,* MC Publishing Co., Glen Rock, N.J. (1993) (hereinafter *McCutcheon's*). Alternatively, the HLB value of a particular surfactant can be estimated by dividing the weight percent of oxyethylene in the surfactant by five (for surfactants including only ethoxy moieties). In addition, the HLB value of a surfactant blend can be determined by the following formula:

$$HLB=(wt.\%A)(HLB_A)+(wt.\%B)(HLB_B)$$

wherein wt. % A and wt. % B are the weight percent of surfactants A and B in the silicon-free surfactant blend, and $HLB_A$ and $HLB_B$ are the HLB values for surfactants A and B, respectively.

Exemplary classes of nonionic surfactants include, but are not limited to, polyoxyethylene ethers of fatty ($C_6$–$C_{22}$) alcohols, polyoxypropylene ethers of fatty ($C_6$–$C_{22}$) alcohols, ethoxylated alkylphenols, polyethylene glycol ethers of methyl glucose, polyethylene glycol ethers of sorbitol, and mixtures thereof.

Prior water-in-oil emulsions incorporating a topically-active compound relied upon a silicon-containing surfactant to serve as an emulsifier. Conventionally, prior water-in-oil emulsions incorporated DOW CORNING 3225C FORMULATION AID, available from Dow Corning Co., Midland, Mich. This silicon-containing surfactant is a dimethicone copolyol, which is a dimethylsiloxane polymer having polyoxyethylene and/or polyoxypropylene side chains. Dimethicone polyols conventionally are used in topically-effective compositions because the silicon-containing surfactants have a low skin irritancy potential. In contrast, some low HLB surfactants exhibit a high skin irritancy potential, and therefore have not been used as a primary emulsifier for water-in-oil emulsions directed to topically-applied products.

In accordance with an important feature of the present invention, silicon-containing surfactants are not a necessary ingredient in a topically-effective composition having a low skin irritancy potential. Highly stable water-in-oil emulsions having a high water content and a low skin irritancy potential can be prepared by incorporating a surfactant phase consisting essentially of silicon-free nonionic surfactants, or blends thereof, having an HLB value of about 0.1 to about 10.

Exemplary silicon-free, nonionic surfactants are the ethoxylated alcohols having an HLB value of about 0.1 to about 10. An especially preferred ethoxylated alcohol is laureth-1, i.e., lauryl alcohol ethoxylated with an average of one mole of ethylene oxide. Other suitable ethoxylated alcohols include laureth-2, laureth-3 and laureth-4. Numerous other nonionic surfactants having an HLB of about 0.1 to about 10 are listed in *McCutcheon's* at pages 229–236, incorporated herein by reference. Other exemplary silicon-free nonionic surfactants having an HLB value of about 0.1 to about 10 include, but are not limited to, the ethoxylated nonylphenols, ethoxylated octylphenols, ethoxylated dodecylphenols, ethoxylated fatty ($C_6$–$C_{22}$) alcohols having 4 or fewer ethylene oxide moieties, oleth-2, steareth-3, steareth-2, ceteth-2, oleth-3, and mixtures thereof.

The surfactant phase also can consist essentially of a silicon-free surfactant blend having an HLB value of about 1 to about 10. The blend is a mixture of a sufficient amount of a silicon-free nonionic surfactant having a low HLB value, i.e., about 0.1 to about 10, and a sufficient amount of a silicon-free nonionic surfactant having a higher HLB value, i.e., about 1 to greater than about 10, such that the surfactant blend has an HLB value of about 1 to about 10. Exemplary, but nonlimiting, silicon-free, nonionic surfactants having a high HLB value are listed in *McCutcheon's* at pages 236–246, incorporated herein by reference.

Exemplary silicon-free, nonionic surfactants having an HLB value greater than about 10 are oleth-10, octylphenol or nonylphenol ethoxylated with six or more moles of ethylene oxide, steareth-10, trideceth-6, methyl gluceth-10, dodoxynol-12, ceteth-12, pareth-20, and mixtures thereof. The identity of the high HLB surfactant is not limited as long as the resulting surfactant phase provides a stable water-in-oil emulsion.

In accordance with an important feature of the present invention, the hydrophobic moiety of the low HLB surfactant is sufficiently soluble in the organic phase such that a sufficient amount of the low HLB surfactant is present in the organic phase to stabilize the water-in-oil emulsion. When the organic phase comprises a silicone compound, the hydrophobic moiety of the low HLB surfactant preferably has about ten to about fourteen carbon atoms. If the hydrophobic moiety includes more than about 14 carbon atoms, the silicon-free surfactant is insoluble in the organic phase and the water-in-oil emulsion is unstable. If the hydrophobic moiety includes less than about 10 carbon atoms, the water-in-oil emulsion has a tendency to coalesce, i.e., the emulsion droplets fuse to form large droplets.

A sufficient amount of surfactant phase in the composition provides a roll-on to gel composition of desired consistency. The amount of surfactant phase necessary to provide a composition of desired consistency varies with the amount of aqueous phase in the composition and is easily determined by those skilled in the art.

A topically-effective composition of the present invention has a viscosity of about 1000 to about 100,000 cps. For a roll-on antiperspirant composition, a sufficient amount of surfactant phase is present in the topically-effective composition if the composition has a viscosity of at least about 1000 cps, and preferably about 1000 to about 3000 cps. A more preferred viscosity for a roll-on topically-effective composition is about 1500 to about 3000 caps. For a gel topically-effective composition, a sufficient amount of surfactant phase is present in the antiperspirant composition if the composition has a viscosity of about 3,000 to about 100,000 cps, and preferably about 3,000 to about 40,000 cps (as measured on a Brookfield Viscometer with a #6 spindle at 5 rpm).

Therefore, the surfactant phase provides water-in-oil emulsions that are useful as non-whitening topically-effective compositions. The water-in-oil emulsions are stable and include a high water content. The present water-in-oil emulsions are stable even when the aqueous phase incorporates a high concentration of topically-active compounds, like antiperspirant salts and/or other water-soluble salts and solutes. These silicon-free surfactants are particularly suitable for emulsifying a high ionic strength aqueous phase in volatile or nonvolatile silicone compounds. The flow properties of the present water-in-oil emulsions are controlled by a judicious selection of the amount of surfactant, as well as the amount of aqueous phase, in the composition.

The present roll-on or gel topically-effective compositions preferably are transparent. However, opacifying agents, pearlescent agents or fillers (e.g., titanium dioxide or a styrene-acrylamide copolymer) that render the composition nontransparent also can be included in the composition if an opaque composition is desired. The presence of such ingredients does not adversely effect the efficacy of the composition and are added to achieve a desired esthetic effect. Preferably, however, the topically-effective compositions are made transparent by intentionally incorporating a refractive index-adjusting compound in the composition to match the refractive indices of the aqueous phase and organic phase.

A water-clear, transparent water-in-oil emulsion is prepared by matching the refractive indices of the aqueous and organic phases at all wavelengths in the visible spectrum. In contrast, if the optical dispersion of the two phases is made to be dissimilar, and the refractive indices are made to match at only one wavelength in the visible spectrum, a transparent chromatic emulsion is prepared. A "chromatic emulsion" transmits a band of wavelengths around the refractive index matching point and scatters the complementary color (i.e., the Christiansen effect).

The refractive index and optical dispersion of the aqueous phase is adjusted by incorporating a suitable water-soluble compound in the aqueous phase or a suitable oil-soluble compound in the organic phase. The refractive index-adjusting compound however must not adversely affect emulsion stability. Water-soluble salts, such as calcium chloride, sodium chloride and zinc chloride, are suitable for use in combination with the topically-active compound to adjust the refractive index of the aqueous phase. Other suitable water-soluble compounds for refractive index matching include potassium iodide, zinc phenylsulfonate and various sugars. A phenyltrimethicone, like DOW CORNING 556 FLUID, is suitable to adjust the refractive index of the organic phase.

In accordance with an important feature of the present invention, and as explained in detail hereinafter, when calcium chloride is added to the aqueous phase as the compound to match the refractive indices of the aqueous and organic phases, the resulting topically-effective composition has a reduced skin irritancy potential. Therefore, the surfactant phase can be essentially free of silicon. Conventionally, expensive silicone surfactants are used to prepare water-in-oil emulsions because silicon-containing surfactants are less irritating to the skin than silicon-free surfactants having a low HLB value, such as laureth-1.

The present topically-effective compositions are non-irritating, water-in-oil emulsions prepared from (a) a silicon-free, low HLB surfactant having no appreciable solubility in the aqueous phase; or (b) a combination of a silicon-free, low HLB surfactant and a silicon-free, high HLB surfactant. The absence of a silicone surfactant achieves cost savings without sacrificing a low skin irritation potential. The topically-effective compositions are non-whitening if a nonvolatile organic compound is included in the organic phase.

The present topically-effective compositions are very high internal phase emulsions comprising about 65% to over 99% aqueous internal phase. By refractive index matching, transparent and, if desired, chromatic emulsions are prepared to provide a desired esthetic appearance. Heretofore, transparency has been difficult to achieve in roll-on or gel topically-effective compositions, and a chromatic effect has been achieved by adding a dye or a pigment to the composition. The irritation potential of the transparent topically-effective composition is reduced by incorporating calcium chloride into the aqueous phase to match the refractive indices of the aqueous and organic phases.

The present water-in-oil emulsions have the benefit of a high aqueous internal phase, but which provide the sensory attributes of an oil-based formulation while incorporating a small amount of organic phase (i.e., the compositions do not feel wet or sticky on application). By refractive index matching, consumer-acceptable transparent emulsions are produced. Regardless of the optical properties of the topically-effective compositions, the emulsion is non-whitening upon application to the skin when the composition includes a nonvolatile organic compound.

The transparent, roll-on or gel topically-effective compositions of the present invention are manufactured by simply admixing composition ingredients at room temperature. Contrary to prior methods of manufacturing roll-on or gel topically-effective compositions, the elevated temperatures needed to melt the thickening agents, and the long cooling times to provide the topically-effective composition, are not required.

A topically-effective composition of the present invention is prepared by admixing the organic phase and the surfactant phase. The topically-active compound is admixed with water to form the aqueous phase. If a transparent composition is desired, a water-soluble compound, such as calcium chloride or a sugar, is added to the aqueous phase in a sufficient amount such that the refractive index of the aqueous phase matches the refractive index of the organic phase. Alternatively, a refractive index-adjusting compound can be added to the organic phase. The aqueous phase then is admixed with the combined organic and surfactant phases. The resulting mixture is stirred until a stable water-in-oil emulsion is prepared. The resulting emulsion finally is introduced into a suitable container.

The following specific examples are illustrative of the topically-effective compositions of the present invention. However, the present invention is not limited to the specific examples set forth below. By varying the proportions and the type of each of the essential ingredients within the above-indicated ranges, a composition of the present invention can be prepared in a liquid or flowable semisolid form. In the following examples, all amounts of the various ingredients are expressed by weight percentages unless otherwise specified.

As demonstrated in the following examples, the topically-effective compositions were transparent and phase-stable over the life of the product; were viscous; and were easy to apply and effectively delivered the topically-active compound to the skin. Each of the following examples was prepared by the above-described method.

EXAMPLE 1

| Ingredient[1] | |
| --- | --- |
| Antiperspirant Compound[2] | 32.9 |
| Water[3] | 32.9 |
| Organic Phase[4] | 28.8 |
| Surfactant Phase[5] | 5.4 |

[1] the amount of each ingredient is expressed as % by weight of the total composition, all percents set forth the amount of each ingredient present in the composition;
[2] aluminum chlorohydrate (ACH), available commercially as CHLOROHYDROL, from Reheis, Inc. Berkeley Heights, New Jersey, added as a 50% weight percent solution of ACH in water;
[3] added as a component of the ACH;
[4] cyclomethicone, available commercially as DOW CORNING FLUID 344, from Dow Corning Co., Midland, MI., added as a 100% active material; and
[5] laureth-1, available commercially as LIPOCOL-1, from Lipo Chemicals, Inc., Paterson, NJ, added as a 100% active material.

The composition of Example 1 was prepared by admixing the composition ingredients, then emulsifying the ingredients in a vortex mixer. The composition of Example 1 was a transparent emulsion that transmits red light and scatters green light. The composition was a flowable gel-like composition which spread easily on the skin and dried quickly, leaving behind a film. The film had a very slight tack. The composition of Example 1 was phase stable, although some emulsified water droplets settled allowing a layer of the continuous organic phase to form at the top of the composition during storage. A simple shake redispersed the aqueous phase.

EXAMPLE 2

| Ingredient[1] | |
| --- | --- |
| Antiperspirant Compound[2] | 40 |
| Water[3] | 40 |
| Organic Phase[4] | 16 |
| Surfactant Phase[5] | 4 |

The composition of Example 2 was prepared in an identical manner as the composition of Example 1. The composition of Example 2 exhibits essentially identical esthetic features as the composition of Example 1. The composition of Example 2 was water clear and only a very small film of organic phase was observed at the top of the water-in-oil emulsion after sitting overnight.

The compositions of Examples 1 and 2 have shown that a surfactant phase consisting essentially of laureth-1 (HLB value about 3.7) adequately resists coalescence of water droplets, but results in a film of the organic phase forming at the top of the emulsion due to settling of the water droplets. In an attempt to overcome this slight tendency of the water droplets to settle, in Example 3 steareth-2 was substituted for the laureth-1 used in the composition of Example 2. Steareth-2, or polyoxyethylene(2) stearyl ether, i.e., BRIJ 72, available commercially from ICI Americas, Inc., Wilmington, Del., as a 100% active material, however was insoluble in the cyclomethicone organic phase at room temperature, and was only 0.8% by weight soluble at 90° C. The resulting emulsion therefore separated. Accordingly, when the organic phase comprises a relatively high amount of a silicone (i.e., at least 25% by weight of the organic phase), the surfactant phase then consists essentially of a silicon-free surfactant having a hydrophobic moiety comprising about 10 to about 14 carbon atoms and having an HLB value of about 0.1 to about 7.

COMPARATIVE EXAMPLE 1

| Ingredient[1] | |
| --- | --- |
| Antiperspirant Compound[2] | 36.5 |
| Water[3] | 36.5 |
| Organic Phase[4] | 16 |
| Surfactant Phase[6] | 11 |

[6] A combination of 6% laureth-1 and 5% dimethicone copolyol, available commercially as SILWET L-77 from Union Carbide Corp., Tarrytown, NY, as a 100% active material.

The composition of Comparative Example 1 was prepared in an identical manner as the composition of Example 1. The composition of Comparative Example 1 was a transparent water-in-oil emulsion which incorporated a silicone surfactant. The composition of Comparative Example 1 was stable after centrifuging 20 minutes at 2900 rpm. After centrifuging, 1.55% of the composition was drawn off as a small oil layer on top due to settling of the emulsion. A temperature stability test was performed on the composition of Comparative Example 1 in a water bath. The emulsion of Comparative Example 1 completely broke at 36.6° C. A second comparative composition incorporating 22% organic phase (cyclomethicone), 2.3% dimethicone copolyol and 2.5% laureth-1 was prepared. This comparative example was opaque and incorporated approximately one-half as much surfactant as incorporated into Comparative Example 1. This second emulsion broke at 45° C. Therefore, a change in the surfactant composition improved the temperature stability of the emulsion.

Prior emulsified compositions incorporated silicone surfactants because low HLB surfactants such as laureth-1 have a high skin irritancy potential. As demonstrated hereinafter, a composition of the present invention can exclude a silicone surfactant and surprisingly maintain a low skin irritancy potential. It also should be understood that a silicone surfactant does not adversely affect a composition of the present invention, and can be added as an optional ingredient. However, the silicone surfactant does not provide any added benefits.

Amine-terminated polydimethylsiloxanes (PS510 and PS513, available from Huls America, Piscataway, N.J. as 100% active materials) were used alone and in combination with laureth-1 as the surfactant phase. Using the amine-terminated polydimethylsiloxane alone and in an amount of 0.1% to 0.8% by weight of the composition provided an emulsified composition having a lumpy consistency. A surfactant phase consisting essentially of PS510 and laureth-1 in various weight percentages (1% through 6%) yielded stable, transparent emulsions when the weight fraction of the aqueous phase (50% ACH/50% water) was 85%. However, the PS510 did not improve the emulsion stability of the composition over a composition utilizing only laureth-1 as the surfactant phase. This was demonstrated in three emulsions containing 3.00% laureth-1 and either 0.037%, 0.47% or 0.55% PS510. The three emulsions were all transparent and had no observable oil layer after sitting for three days. After centrifuging, the observable oil layer accounted for about 2.5% of the total composition. A composition incorporating PS510 or PS513 therefore did not improve the stability of the composition.

In accordance with an important feature of the present invention, the weight percent of the aqueous phase is maintained at a high level and the aqueous phase is used to match the refractive indices of the aqueous and the organic phases. Various water-soluble compounds were added to the aqueous phase to match the refractive indices of the phases. The identity of the water-soluble compound is not limited as long as the stability, the efficacy and the esthetics of the water-in-oil emulsion are not adversely affected.

In one experiment a composition containing a 76% (by weight) aqueous phase, a 21% organic phase (polyphenylmethylsiloxane) and a 3.4% surfactant phase (laureth-1) was prepared. The aqueous phase comprised 17% water, 17% antiperspirant compound, 33% polyethylene glycol (PEG-4) and 33% glycerin. The emulsion was unstable. Similarly, an aqueous phase comprising polyethylene glycol, water and an antiperspirant compound was unstable. The instability of these emulsions was attributed to the high polyethylene glycol content which affected the solubility of the surfactant phase in the aqueous phase. Accordingly, a polyethylene glycol can be used at a low concentration (i.e., less than about 10%) to match the refractive indices of the aqueous and organic phases, but is unsuitable at high concentrations. Exemplary, but nonlimiting, water-soluble compounds are sugars, calcium chloride and zinc chloride.

Using water, as opposed to a water-soluble compound, to increase the weight percent of the aqueous phase results in an opaque, stable emulsion that exhibits very low syneresis during storage. The composition of Example 4 is illustrative of such a composition.

EXAMPLE 4

| Ingredient[1] | |
|---|---|
| Antiperspirant Compound[2] | 28 |
| Water | 57 |
| Organic Phase[4] | 11 |
| Surfactant Phase[5] | 4 |

Compositions including a relatively low amount of antiperspirant compound are termed deodorants as opposed to antiperspirants. Deodorant compositions also can be made consumer acceptable by incorporating an appropriate amount of surfactant phase and water-soluble compound into the composition. The addition of a suitable water-soluble compound provides a transparent composition, as illustrated in Examples 5 and 6.

EXAMPLE 5

| Ingredient[1] | |
|---|---|
| Antiperspirant Compound[2] | 28 |
| Water | 46.85 |
| Calcium Chloride | 10.15 |
| Organic Phase[4] | 11 |
| Surfactant Phase[5] | 4 |

The composition of Example 5 was prepared in an identical manner as the composition of Example 1. The composition of Example 5 was transparent and stable. The aqueous phase of the composition of Example 5 contained 32.94% antiperspirant compound, 55.12% water and 11.94% calcium chloride, and had a refractive index of 1.394. The organic phase had a refractive index of 1.394.

EXAMPLE 6

| Ingredient[1] | |
|---|---|
| Antiperspirant Compound[2] | 29 |
| Water | 45.5 |
| Calcium Chloride | 5.5 |
| Organic Phase[7] | 16.2 |
| Surfactant Phase | 3.8 |

[7]10.6% DOW CORNING 344 FLUID and 5.6% DOW CORNING 200 FLUID (0.65 centistoke), a volatile, linear polydimethylsiloxane fluid available from Dow Corning Corporation, Midland, MI.

The composition of Example 6 was prepared in an identical manner to the composition of Example 1. The composition of Example 6 was transparent and stable, transmitting yellow light and scattering purple light. The composition of Example 6 can be pumped and sprayed in a non-aerosol package. The aqueous phase of the composition of Example 6 contained 36.25% antiperspirant compound, 6.88% calcium chloride and 56.87% water.

The composition of Example 6 exhibited improved esthetic properties over the composition of Example 5. The composition of Example 6 had a reduced tackiness and flakiness. The improved esthetic features were attributed to a reduction in the amount of calcium chloride and the inclusion of the linear polymethylsiloxane in the composition.

In addition to being esthetically-pleasing to the consumer, a topically-effective composition also: (1) must effectively deliver the topically-active composition to the skin or hair and (2) must not irritate the contacted area of the skin. Typically, low HLB surfactants have not been included in topically-effective compositions because they are skin irritants. Costly silicone surfactants can be included in topically-effective compositions because these surfactants have a low skin irritancy potential. In accordance with an important feature of the present invention, economical silicon-free, nonionic surfactants having a low HLB value can be included in the topically-active compositions to provide a composition having a low skin irritancy potential.

In particular, in a forearm screening test used to assess antiperspirant efficiency, four different compositions were applied to the forearms of test panelists. The four tested compositions were:

(a) 56% (by weight) CHLOROHYDROL, 29% aqueous calcium chloride solution (35%), 14% DOW CORNING 344 FLUID and 1% laureth-1;

(b) 56% (by weight) CHLOROHYDROL, 29% aqueous calcium chloride solution (35%), 10% DOW CORNING 344 FLUID and 5% laureth-1;

(c) 56% (by weight) CHLOROHYDROL, 29% water, 14% DOW CORNING 344 FLUID and 1% laureth-1; and (d) 56% (by weight) CHLOROHYDROL, 29% water, 10% DOW CORNING 344 FLUID and 5% laureth-1.

In the standardized test, no irritation was observed on the forearm test sites corresponding to composition (a) for any panelist. Compositions (a) and (b), which include calcium chloride, exhibited a reduced skin irritancy potential compared to compositions (c) and (d) that do not include calcium chloride. Therefore, surprisingly, a composition of the present invention that incorporates calcium chloride into the aqueous phase to match the refractive index of the organic phase, demonstrates a reduced skin irritancy potential and allows use of a silicon-free surfactant as the surfactant phase.

In addition to antiperspirant compositions, other topically-effective compositions can be prepared. The topically-effective compositions comprise a topically-active compound, such as a skin care compound, a sunscreen or a topical medicament. The compositions of Examples 7 through 23, summarized in Table 1, illustrate other topically-effective compositions of the present invention.

In Examples 7 through 23, the organic phase was DOW CORNING 344 FLUID. The surfactant phase was a combination of laureth-1 and laureth-4. In preparing the composition of Examples 7 through 23, the DOW CORNING 344 FLUID, laureth-1 and laureth-4, in a weight ratio of 7:2:1, respectively, were admixed until homogeneous. The resulting solution had a refractive index of 1.41257, as measured on an ABBE High Accuracy 60/ED Refractometer, available from Bellingham & Stanley Ltd., England.

The aqueous phase included water, the topically-active compound and sufficient sugar to match the refractive index of the organic phase. The aqueous phase was 80% by weight of the composition. Admixing the aqueous phase with the solution of the organic phase and the surfactant phase provided a clear, stable water-in-oil emulsion. Transparency was achieved by matching the refractive index of aqueous and organic phases. Refractive index matching was accomplished by adjusting the amount of sugar in the water phase of the composition. Table 1 summarizes the final weight percent of each ingredient present in the compositions of Examples 7 through 23, the final use of the topically-effective composition, and physical properties of the compositions.

TABLE 1

| | Aqueous Phase | | | Organic Phase | Surfactant Phase | | Composition | | |
|---|---|---|---|---|---|---|---|---|---|
| Ex. | % sugar (by weight) | Topically-effective compound | % topically-effective compound | % water | % cyclo-methicone | % laureth-1 | % laureth-4 | Product Type | Stability | Appearance (after one week) |
| 7 | 36.4% | Hyaluronic acid | 0.13% | 44.1% | 13.6% | 3.88% | 1.94% | night cream | stable | clear, an oil layer on top |
| 8 | 29.0% | sodium salicylate | 3.90% | 47.0% | 14.0% | 4.00% | 2.00% | night cream | stable | clear, an oil layer on top |
| 9 | 31.8% | Urea | 7.60% | 47.1% | 9.49% | 2.70% | 1.35% | night cream | stable | clear, an oil layer on top |
| 10 | 35.5% | 85% lactic acid | 4.90% | 45.0% | 10.2% | 2.93% | 1.46% | night cream | stable | clear, an oil layer on top |
| 11 | 33.4% | 5% glycerin | 3.60% | 46.8% | 11.3% | 3.24% | 1.62% | night cream | stable | clear, an oil layer on top |
| 12 | 32.2% | Vitamin C | 4.29% | 45.1% | 12.9% | 3.69% | 1.84% | water-soluble vitamin | stable | clear, an oil layer on top |
| 13 | 35.3% | Vitamin $B_1$ | 0.59% | 45.0% | 13.4% | 3.83% | 1.92% | water-soluble vitamin | stable | clear, an oil layer on top |
| 14 | 34.3% | pyridoxine hydrochloride | 1.32% | 45.1% | 13.5% | 3.87% | 1.94% | water-soluble vitamin | stable | clear, an oil layer on top |
| 15 | 37.1% | panthenol | 1.90% | 46.3% | 10.3% | 2.95% | 1.47% | water-soluble vitamin | stable | clear, an oil layer on top |
| 16 | 35.7% | nicotinic acid | 0.42% | 44.5% | 13.6% | 3.88% | 1.94% | cosmetic | stable | clear, an oil layer on top |
| 17 | 35.7% | boric acid | 1.08% | 43.8% | 13.7% | 3.90% | 1.95% | medicament | stable | clear, an oil layer on top |
| 18 | 34.9% | sodium sulfactamide | 2.74% | 48.5% | 9.70% | 2.77% | 1.39% | bacteriocide | stable | clear, an oil layer on top |

TABLE 1-continued

| | Aqueous Phase | | | Organic Phase | Surfactant Phase | | Composition | | |
|---|---|---|---|---|---|---|---|---|---|
| Ex. | % sugar (by weight) | Topically-effective compound | % topically-effective compound | % water | % cyclo-methicone | % laureth-1 | % laureth-4 | Product Type | Stability | Appearance (after one week) |
| 19 | 32.5% | triclosan | 1.03% | 37.6% | 20.2% | 5.77% | 2.88% | bacteriocide | stable | clear, an oil layer on top |
| 20 | 37.6% | indomethacin | 1.90% | 43.4% | 12.8% | 2.91% | 1.43% | anti-inflammatory agent | stable | cloudy, an oil layer on top |
| 21 | 39.1% | 87% bisabolol | 0.70% | 45.1% | 10.6% | 3.03% | 1.51% | anti-irritant | stable | clear, an oil layer on top |
| 22 | 31.9% | silver sulfodizine | 3.30% | 36.8% | 19.6% | 5.61% | 2.81% | medicament | stable | cloudy, an oil layer on top |
| 23 | 37.2% | hydroxyethyl cellulose | 0.26% | 50.1% (0.57 mM KOH) | 8.70% | 2.48% | 1.24% | water-soluble polymer | stable | clear, an oil layer on top |

A transparent, roll-on or gel topically-effective composition of the present invention demonstrates excellent esthetic and functional properties, such as transparency, pay-off (i.e., ability to deliver the antiperspirant compound), viscosity and low tack. The compositions exhibited an excellent stability at room temperature and are essentially syneresis free.

The topically-effective compositions of the present invention exhibit unique and superior properties upon topical application to skin. The improved physical and sensory properties include a sufficient viscosity to effectively deliver the topically-effective compound to the skin; storage stability; elimination of the vigorous shaking requirement to redistribute the topically-effective compound prior to use; reduced or no whitening of the skin and clothing after topical application; and transparency for enhanced consumer acceptance. The topically-effective compositions are non-oily after topical application; dry quickly after topical application; and exhibit improved efficacy and sensory properties.

It should be understood that the foregoing detailed description is given merely by way of illustration. Obviously, many modifications and variations of the invention as hereinbefore set forth can be made without departing from the spirit and scope thereof and therefore only such limitations should be imposed as are indicated by the appended claims.

What is claimed and desired to be secured by Letters Patent is:

1. An emulsified, water-in-oil antiperspirant composition comprising:
   (a) about 65% to about 99.5% by weight of the composition of an aqueous phase, said aqueous phase comprising
      (i) about 1% to about 40% by weight of the composition of an antiperspirant compound and
      (ii) water;
   (b) about 0.5% to about 35% by weight of the composition of an organic phase comprising a volatile silicone compound, a volatile hydrocarbon compound, or a mixture thereof; and
   (c) about 0.1% to about 15% by weight of the composition of a surfactant phase consisting essentially of a surfactant or a surfactant blend, wherein the surfactant or surfactant blend has an HLB value of about 10 or less and is free of silicon, and wherein the surfactant phase comprises a nonionic surfactant selected from the group consisting of a polyoxyethylene ether of a fatty ($C_6$–$C_{22}$) alcohol, an ethoxylated alkylphenol, a polyethylene glycol ether of methyl glucose, a polyethylene glycol ether of sorbitol, and mixtures thereof.

2. The composition of claim 1 further comprising a refractive index-adjusting compound to match the refractive index of the aqueous phase to the refractive index of the organic phase and provide a transparent composition.

3. The composition of claim 2 wherein the composition has a % of transmittance at 700 nm of at least 50%.

4. The composition of claim 1 wherein the composition is a liquid or a flowable semisolid having a viscosity of about 1,000 to about 100,000 centipoise.

5. The composition of claim 1 wherein the antiperspirant compound is present in an amount of about 5% to about 30% by weight of the composition.

6. The composition of claim 1 wherein the antiperspirant compound is present in an amount of about 10% to about 25% by weight of the composition.

7. The composition of claim 1 wherein the antiperspirant compound is an astringent salt comprising aluminum, zirconium, zinc or a mixture thereof.

8. The composition of claim 1 wherein the antiperspirant compound is selected from the group consisting of aluminum bromohydrate, potassium alum, sodium aluminum chlorohydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof.

9. The composition of claim 1 wherein the organic phase is present in an amount of about 2% to about 20% by weight of the composition.

10. The composition of claim 1 wherein the volatile silicone compound has a viscosity of about 0.5 to about 6 centistokes.

11. The composition of claim 1 wherein the volatile silicone compound comprises a cyclic volatile silicone having a viscosity at 25° C. of about 2 to about 6 centistokes and a boiling point at 760 mm of about 150° C. to about 250° C.

12. The composition of claim 11 wherein the cyclic volatile silicone is a cyclomethicone.

13. The composition of claim 12 wherein the cyclomethicone is selected from the group consisting of hexamethylcyclotrisiloxane, octamethylcyclotetrasiloxane, decamethylcyclopentasiloxane, dodecamethylcyclohexasiloxane, and mixtures thereof.

14. The composition of claim 1 wherein the volatile silicone compound comprises a linear volatile silicone having a viscosity at 25° C. of about 0.5 to about 5 centistokes and a boiling point at 760 mm of about 100° C. to about 250° C.

15. The composition of claim 14 wherein the linear volatile silicone is selected from the group consisting of hexamethyldisiloxane, octamethyltrisiloxane, decamethyltetrasiloxane, dodecamethylpentasiloxane, bisphenylhexamethicone, and mixtures thereof.

16. The composition of claim 1 wherein the volatile hydrocarbon compound has about 10 to about 30 carbon atoms.

17. The composition of claim 16 wherein the volatile hydrocarbon compound has about 12 to about 24 carbon atoms and has a boiling point at 760 mm of about 100° C. to about 250° C.

18. The composition of claim 1 wherein the volatile hydrocarbon compound has the structural formula:

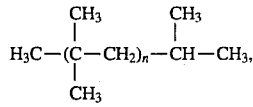

wherein n ranges from 2 to about 5, and mixtures.

19. The composition of claim 1 wherein the organic phase further comprises a nonvolatile organic compound.

20. The composition of claim 19 wherein the nonvolatile organic compound is selected from the group consisting of a mineral oil, phenyltrimethicone, a polydimethylsiloxane having a viscosity at 25° C. of about 6 to about 400 cs, an ester having about 10 to about 32 carbon atoms, 1-decene dimer, a polydecene, isoeicosane, a hydrogenated polybutene, and mixtures thereof.

21. The composition of claim 1 wherein the surfactant phase is present in an amount of about 0.1% to about 10% by weight of the composition.

22. The composition of claim 1 wherein the surfactant phase is present in an amount of about 0.5% to about 5% by weight of the composition.

23. The composition of claim 1 wherein the surfactant phase has an HLB value of about 0.1 to about 10.

24. A method of treating or preventing malodors associated with human perspiration comprising topically applying an effective amount of an antiperspirant composition to human skin, said composition comprising:
(a) about 65% to about 99.5% by weight of the composition of an aqueous phase, said aqueous phase comprising
(i) about 1% to about 40% by weight of the composition of an antiperspirant compound and
(ii) water;
(b) about 0.5% to about 35% by weight of the composition of an organic phase comprising a volatile silicone compound, a volatile hydrocarbon compound, or a mixture thereof; and
(c) about 0.1% to about 15% by weight of the composition of a surfactant phase consisting essentially of a surfactant or a surfactant blend, wherein the surfactant or surfactant blend has an HLB value of about 10 or less and is free of silicon, and wherein the surfactant phase comprises a nonionic surfactant selected from the group consisting of a polyoxyethylene ether of a fatty ($C_6$–$C_{22}$) alcohol, an ethoxylated alkylphenol, a polyethylene glycol ether of methyl glucose, a polyethylene glycol ether of sorbitol, and mixtures thereof.

25. An emulsified, water-in-oil antiperspirant composition comprising:
(a) about 65% to about 99.5% by weight of the composition of an aqueous phase, said aqueous phase comprising
(i) about 1% to about 40% by weight of the composition of an antiperspirant compound and
(ii) water;
(b) about 0.5% to about 35% by weight of the composition of an organic phase comprising a volatile silicone compound, a volatile hydrocarbon compound, or a mixture thereof; and
(c) about 0.1% to about 15% by weight of the composition of a surfactant phase consisting essentially of a surfactant or a surfactant blend, wherein the surfactant or surfactant blend has an HLB value of about 1 to about 7 and is free of silicon, and wherein the surfactant phase comprises a nonionic surfactant selected from the group consisting of a polyoxyethylene ether of a fatty ($C_6$–$C_{22}$) alcohol, an ethoxylated alkylphenol, a polyethylene glycol ether of methyl glucose, a polyethylene glycol ether of sorbitol, and mixtures thereof.

26. An emulsified, water-in-oil antiperspirant composition comprising:
(a) about 65% to about 99.5% by weight of the composition of an aqueous phase, said aqueous phase comprising
(i) about 1% to about 40% by weight of the composition of an antiperspirant compound and
(ii) water;
(b) about 0.5% to about 35% by weight of the composition of an organic phase comprising a volatile silicone compound, a volatile hydrocarbon compound, or a mixture thereof;
(c) about 0.1% to about 15% by weight of the composition of a surfactant phase consisting essentially of a surfactant or a surfactant blend, wherein the surfactant or surfactant blend has an HLB value of about 10 or less and is free of silicon, and wherein the surfactant phase comprises a nonionic surfactant selected from the group consisting of a polyoxyethylene ether of a fatty ($C_6$–$C_{22}$) alcohol, an ethoxylated alkylphenol, a polyethylene glycol ether of methyl glucose, a polyethylene glycol ether of sorbitol, and mixtures thereof; and
(d) an oil-soluble refractive index-adjusting compound to match the refractive index of the aqueous phase to the refractive index of the organic phase and provide a transparent composition.

27. An emulsified, water-in-oil antiperspirant composition comprising:
(a) about 65% to about 99.5% by weight of the composition of an aqueous phase, said aqueous phase comprising
(i) about 1% to about 40% by weight of the composition of an antiperspirant compound comprising aluminum chlorohydrate and
(ii) water;
(b) about 0.5% to about 35% by weight of the composition of an organic phase comprising cyclomethicone; and (c) about 0.1% to about 15% by weight of the composition of a surfactant phase consisting essentially of laureth-1.

28. The composition of claim 25 wherein the surfactant phase has an HLB value of about 3 to about 6.

29. The composition of claim 1 wherein the surfactant phase consists essentially of a single silicon-free surfactant having an HLB value of about 0.1 to about 10.

30. The composition of claim 1 wherein the surfactant phase consists essentially of a silicon-free surfactant blend having an HLB value of about 1 to about 10, said surfactant blend comprising a first surfactant having an HLB value of about 0.1 to about 10 and a second surfactant having an HLB greater than about 10.

31. The composition of claim 1 wherein the surfactant phase is selected from the group consisting of laureth-1, laureth-2, laureth-3, laureth-4, oleth-2, steareth-3, steareth-2, ceteth-2, oleth-3, an ethoxylated nonylphenol, ethoxylated octylphenol, ethoxylated dodecylphenol, ethoxylated fatty ($C_6$–$C_{22}$) alcohol having 4 or fewer ethylene oxide moieties, and mixtures thereof.

32. The composition of claim 1 wherein the organic phase comprises a volatile silicone compound and the surfactant phase consists essentially of a silicon-free surfactant having a hydrophobic moiety having about 10 to about 14 carbon atoms.

33. The composition of claim 2 wherein the refractive index-adjusting compound is water soluble.

34. The composition of claim 31 wherein the water-soluble refractive index-adjusting compound is selected from the group consisting of calcium chloride, sodium chloride, zinc chloride, potassium iodide, zinc phenylsulfonate, a sugar, and mixtures thereof.

35. The composition of claim 26 wherein the oil-soluble refractive index-adjusting compound comprises a phenyltrimethicone.

36. The composition of claim 27 wherein calcium chloride is added to the aqueous phase to match the refractive index of the aqueous phase to the refractive index of the organic phase.

37. An emulsified, water-in-oil topically-effective composition comprising:
   (a) about 65% to about 99.5% by weight of the composition of an aqueous phase, said aqueous phase comprising:
      (i) a topically-effective amount of a topically-active compound, and
      (ii) water;
   (b) about 0.5% to about 35% by weight of the composition of an organic phase comprising a volatile silicone compound, a volatile hydrocarbon compound, or a mixture thereof; and
   (c) about 0.1% to about 15% by weight of the composition of a surfactant phase consisting essentially of a surfactant or a surfactant blend, wherein the surfactant or surfactant blend has an HLB value of about 10 or less and is free of silicon, and wherein the surfactant phase comprises a nonionic surfactant selected from the group consisting of a polyoxyethylene ether of a fatty ($C_6$–$C_{22}$) alcohol, an ethoxylated alkylphenol, a polyethylene glycol ether of methyl glucose, a polyethylene glycol ether of sorbitol, and mixtures thereof.

38. The composition of claim 37 wherein the topically-active compound is present in an amount of 0.1% to about 40% by weight of the composition.

39. The composition of claim 38 wherein the topically-active compound is selected from the group consisting of a skin care agent, a topical medicament, a topically-effective drug, a topical anesthetic, a sunscreen agent, a topical cosmetic, a topical anti-inflammatory, an antibacterial compound, a dermatological compound, an antifungal compound, and mixtures thereof.

40. An emulsified water-in-oil topically-effective composition comprising:
   (a) about 65% to about 99.5% by weight of the composition of an aqueous phase, said aqueous phase comprising:
      (i) a topically-effective amount of a first topically-active compound, and
      (ii) water;
   (b) about 0.5% to about 35% by weight of the composition of an organic phase comprising:
      (i) a topically-effective amount of a second topically-active compound, and
      (ii) a volatile silicone compound, a volatile hydrocarbon compound, or a mixture thereof; and
   (c) about 0.1% to about 15% by weight of the composition of a surfactant phase consisting essentially of a surfactant or a surfactant blend, wherein the surfactant or surfactant blend has an HLB value of about 10 or less and is free of silicon, and wherein the surfactant phase comprises a nonionic surfactant selected from the group consisting of a polyoxyethylene glycol ether of a fatty ($C_6$–$C_{22}$) alcohol, an ethoxylated alkylphenol, a polyethylene glycol ether of methyl glucose, a polyethylene ether of sorbitol, and mixtures thereof; and
   (d) a refractive index-adjusting compound to match the refractive index of the aqueous phase to the refractive index of the organic phase and provide a transparent composition.

41. An emulsified, water-in-oil topically-effective composition comprising:
   (a) about 65% to about 99.5% by weight of the composition of an aqueous phase, said aqueous phase comprising:
      (i) a topically-effective amount of a topically-active compound, and
      (ii) water;
   (b) about 0.5% to about 35% by weight of the composition of an organic phase comprising a volatile silicone compound, a volatile hydrocarbon compound, or a mixture thereof;
   (c) about 0.1% to about 15% by weight of the composition of a surfactant phase consisting essentially of a surfactant or a surfactant blend, wherein the surfactant or surfactant blend has an HLB value of about 10 or less and is free of silicon, and wherein the surfactant phase comprises a nonionic surfactant selected from the group consisting of a polyoxyethylene ether of a fatty ($C_6$–$C_{22}$) alcohol, an ethoxylated alkylphenol, a polyethylene glycol ether of methyl glucose, a polyethylene glycol ether of sorbitol, and mixtures thereof; and
   (d) a refractive index-adjusting compound to match the refractive index of the aqueous phase to the refractive index of the organic phase and provide a transparent composition.

42. An emulsified, water-in-oil antiperspirant composition comprising:
   (a) about 65% to about 99.5% by weight of the composition of an aqueous phase, said aqueous phase comprising
      (i) about 1% to about 40% by weight of the composition of an antiperspirant compound and
      (ii) water;

(b) about 0.5% to about 35% by weight of the composition of an organic phase comprising a volatile silicone compound, a volatile hydrocarbon compound, or a mixture thereof; and (c) about 0.1% to about 15% by weight of the composition of a surfactant phase consisting essentially of a silicon-free surfactant blend having an HLB value of about 1 to about 10, said surfactant blend comprising a first surfactant having an HLB value of about 0.1 to about 10 and a second surfactant having an HLB greater than about 10.

43. An emulsified, water-in-oil topically-effective composition comprising:

(a) about 65% to about 99.5% by weight of the composition of an aqueous phase, said aqueous phase comprising:

(i) a topically-effective amount of a topically-active compound, and (ii) water;

(b) about 0.5% to about 35% by weight of the composition of an organic phase comprising a volatile silicone compound, a volatile hydrocarbon compound, or a mixture thereof; and (c) about 0.1% to about 15% by weight of the composition of a surfactant phase consisting essentially of a silicon-free surfactant blend having an HLB value of about 1 to about 10, said surfactant blend comprising a first surfactant having an HLB value of about 0.1 to about 10 and a second surfactant having an HLB greater than about 10.

* * * * *